US012629449B2

(12) United States Patent
Link et al.

(10) Patent No.: US 12,629,449 B2
(45) Date of Patent: May 19, 2026

(54) ORTHOPEDIC IMPLANTS WITH INCREASED HARDNESS AND INCREASED DEPTH OF HARDNESS AND METHOD OF MAKING

(71) Applicant: WALDEMAR LINK GMBH & CO. KG, Hamburg (DE)

(72) Inventors: Helmut D. Link, Hamburg (DE); Richard Csaszar, Bad Segeberg (DE)

(73) Assignee: WALDEMAR LINK GMBH & CO. KG, Hamburg (DE)

( * ) Notice: Subject to any disclaimer, the term of this patent is extended or adjusted under 35 U.S.C. 154(b) by 406 days.

(21) Appl. No.: 18/252,216

(22) PCT Filed: Nov. 9, 2021

(86) PCT No.: PCT/EP2021/081167
§ 371 (c)(1),
(2) Date: May 9, 2023

(87) PCT Pub. No.: WO2022/101231
PCT Pub. Date: May 19, 2022

(65) Prior Publication Data
US 2023/0405183 A1     Dec. 21, 2023

Related U.S. Application Data

(60) Provisional application No. 63/233,515, filed on Aug. 16, 2021, provisional application No. 63/111,964, filed on Nov. 10, 2020.

(51) Int. Cl.

| | |
|---|---|
| *A61L 27/30* | (2006.01) |
| *A61L 27/04* | (2006.01) |
| *A61L 27/06* | (2006.01) |
| *A61L 27/50* | (2006.01) |
| *C23C 8/24* | (2006.01) |
| *C23C 8/36* | (2006.01) |
| *C23C 14/02* | (2006.01) |
| *C23C 14/06* | (2006.01) |
| *C23C 14/32* | (2006.01) |
| *A61F 2/30* | (2006.01) |

(52) U.S. Cl.
CPC .......... *A61L 27/306* (2013.01); *A61L 27/045* (2013.01); *A61L 27/047* (2013.01); *A61L 27/06* (2013.01); *A61L 27/50* (2013.01); *C23C 8/24* (2013.01); *C23C 8/36* (2013.01); *C23C 14/02* (2013.01); *C23C 14/0641* (2013.01);

*C23C 14/325* (2013.01); *A61F 2002/30922* (2013.01); *A61F 2002/30971* (2013.01); *A61L 2420/02* (2013.01)

(58) Field of Classification Search
CPC .... A61L 27/306; A61L 27/045; A61L 27/047; A61L 27/06; A61L 27/50; C23C 8/36; C23C 8/24; C23C 14/02; C23C 14/0641; C23C 14/325
See application file for complete search history.

(56) References Cited

U.S. PATENT DOCUMENTS

| | | | |
|---|---|---|---|
| 6,110,571 A | 8/2000 | Yaginuma et al. | |
| 6,117,280 A | 9/2000 | Yaginuma et al. | |

FOREIGN PATENT DOCUMENTS

| | | | | |
|---|---|---|---|---|
| EP | 0320706 A1 | 6/1989 | | |
| EP | 1923079 A1 | 5/2008 | | |
| FR | 2722800 A1 | 1/1996 | | |
| GB | 2227755 A * | 8/1990 | ........... | C23C 14/024 |
| GB | 2443797 A * | 5/2008 | ......... | A61F 2/30767 |
| RU | 2686975 C1 | 5/2019 | | |
| WO | WO-03093527 A1 * | 11/2003 | ............. | A61L 27/50 |
| WO | WO-2005073426 A1 * | 8/2005 | ............... | C23C 8/24 |
| WO | WO-2018081283 A1 * | 5/2018 | ............. | A61L 31/16 |

OTHER PUBLICATIONS

Huchel, U and S. Stramke. "Pulsed Plasma Nitriding of Titanium and Titanium Alloys." https://www.eltropuls.de/wp-content/uploads/2019/10/titan.pdf (Year: 2019).*
International Search Report and Written Opinion mailed Jan. 18, 2022, in connection with International Patent Application No. PCT/EP2021/081167, 10 pgs.

* cited by examiner

*Primary Examiner* — Tima M. McGuthry-Banks

(74) *Attorney, Agent, or Firm* — Chiesa Shahinian & Giantomasi PC

(57) ABSTRACT

A prosthesis or implant device for use in joint or bone repair, or restoration of function, with improved surface hardness and depth of hardness and a process comprising treating a biocompatible alloy such that hardness and depth of hardness is improved.

16 Claims, No Drawings

ORTHOPEDIC IMPLANTS WITH INCREASED HARDNESS AND INCREASED DEPTH OF HARDNESS AND METHOD OF MAKING

CROSS-REFERENCE TO RELATED APPLICATION(S)

This application is a National Stage under 35 U.S.C. 371 of International Patent Application No. PCT/EP2021/081167, filed Nov. 9, 2021, which claims priority to U.S. Provisional Patent Application No. 63/111,964, filed Nov. 10, 2020, and U.S. Provisional Patent Application No. 63/233,515, filed Aug. 16, 2021; the disclosures of all of which are incorporated herein by reference in their entireties.

FIELD OF INVENTION

The invention is associated with the field of orthopedic implants, in particular prostheses and implants for joint replacement, bone repair, and restoration of function.

BACKGROUND OF THE INVENTION

Prostheses are commonly used to repair joints that have lost full or partial function due to damage, disease, or injury. These devices must be made of a biocompatible materials that are both safe and durable. Commonly used metallic biocompatible materials used to make orthopedic implants include, but are not limited to: stainless steels, cobalt alloys, titanium and titanium alloys.

Hardness is a property of a material that will result in increased wear resistance. This is true in the case of orthopedic devices as well—a harder and more durable implant will prevent the device from breaking down over time and can prevent the device from becoming defective, and therefore needing to be replaced. Hardness is measured in the art by the Vickers hardness test. The unit of measurement given is known as the Vickers Pyramid Number ("HV"). There remains a need in the art for harder alloys, and processes by which to increase hardness. These harder alloys, and prosthetics made from them, have great utility in the manufacturer of durable medical devices.

Various surface treatment can increase the hardness of alloys including but not limited to carburizing, self-bath nitrocarburizing, gas nitriding, or pulse plasma nitriding Pulse plasma nitriding involves placing a device inside a vacuum chamber containing a gas mixture that is usually nitrogen, oxygen, hydrogen and/or methane gas. The chamber is pressurized, heated, and then a pulsating DC voltage is applied between the charge (cathode) and the chamber wall (anode). This causes the ionization of the gas in the chamber, which introduces nitrogen into the surface of the implant and causes the nitrogen to diffuse into the material.

Coatings can be applied to metal alloys through various methods. One such method, Arc-PVD, involves the use of a DC Power Supply to apply a focused stream or arc of low voltage and high current electrical energy to heat a small spot on the exterior of the orthopedic device (known as the "cathodic spot") to above its melting point. The heat generated vaporizes the target material and creates a hole in the surface. The arc then extinguishes and reignites closely adjacent to the original spot on the surface of the target, and this process continues forming a series of spot formations, or arcs, across the surface of the device. The arc has high power density and high ionization potential, such that a magnetic field can be applied to the arc which will direct the current around the full target surface and can provide a uniform deposition across the entire cathodic target surface.

SUMMARY OF INVENTION

The present invention is an orthopedic implant with enhanced durability made using a two-step process. During the first step, the orthopedic implant undergoes a surface treatment to enhance both the hardness and depth of hardness of the implant. Then, in a second step, a coating is applied to reduce friction, further improve wear resistance, present a chemical barrier, or apply decorative colors and aesthetics.

Different alloys, already established as safe and effective for use in orthopedic devices, can be treated using this process to increase their hardness and the depth of hardness.

An aspect of this invention is the process for making an orthopedic device with increased surface hardness and increased hardness depth.

Another aspect of this invention is an orthopedic implant with increased surface hardness and increased hardness depth.

In some preferred embodiments, the orthopedic implant can be made from titanium alloys or cobalt chromium molybdenum alloys.

In a preferred embodiment, the surface treatment is pulse plasma nitriding.

In a preferred embodiment, the coating layer is applied using an Arc-PVD process.

In a preferred embodiment, the coating layer added is TiNbN or ZrN.

In preferred embodiments, a cobalt chromium molybdenum orthopedic implant has a surface hardness of between 550 and 1300 HV0.1. In a most preferred embodiment the surface hardness is 1250 HV0.1.

In a preferred embodiment, a titanium/titanium alloy orthopedic implant has a surface hardness of between 200 HV0.1 and 1000 HV0.05. In a most preferred embodiment the surface hardness is 950 HV0.05.

In an embodiment of the invention in which the orthopedic device is made of cobalt chromium molybdenum alloys, the hardness of the orthopedic device reaches a depth of between 15 to 50 micrometers. In a preferred embodiment the depth of hardness is approximately 35 micrometers.

In an embodiment of the invention in which the orthopedic device is made of titanium alloys, the hardness of the orthopedic device reaches a depth of between and 70-micrometers. In a preferred embodiment, the depth of hardness is approximately 40 micrometers.

DETAILED DESCRIPTION OF THE INVENTION

A preferred embodiment of the invention employs pulse plasma nitriding followed by Arc-PVD to increase the surface hardness and depth of hardness of orthopedic implants made of titanium alloys or cobalt chromium molybdenum alloys.

In these preferred embodiments, an orthopedic implant made of CoCrMo undergoes pulse plasma nitriding for 10 to 20 hours at approximately 600 degrees Celsius. In a most preferred embodiment the implant undergoes pulse plasma nitriding for 16 hours at approximately 600 degrees Celsius, achieving a surface hardness of approximately 1250 HV0.1 and a hardness depth of 35 micrometers.

In another embodiment, an orthopedic implant made of TiAl6V4 undergoes pulse plasma nitriding for 10 to 48 hours at approximately 730 to 750 degrees Celsius. In a most preferred embodiment, an orthopedic implant made of TiAl6V4 undergoes pulse plasma nitriding for 16 hours at approximately 730 to 750 degrees Celsius achieving a surface hardness of approximately 950 HV0.05 and a hardness depth of 40 micrometers.

After pulse plasma nitriding, the Arc-PVD process is applied to the orthopedic implants, coating them with a hard material layer of titanium niobium nitride, zirconium nitride, or another substance, with a thickness of 4.5 plus or minus 1.5 micrometers.

The foregoing description is given for clearness of understanding only, and no unnecessary limitations should be understood therefrom, as modifications within the scope of the invention may be apparent to those having ordinary skill in the art.

Detailed embodiments of the present prostheses and implant devices and methods are disclosed herein; however, it is to be understood that the disclosed embodiments are merely illustrative and that the prostheses and implant devices and methods may be embodied in various forms. In addition, each of the examples given in connection with the various embodiments of the systems and methods are intended to be illustrative, and not restrictive.

Throughout this disclosure, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various steps may be changed without departing from the scope or spirit of the method, unless described otherwise. In addition, some of the individual steps can be combined, omitted, or further subdivided into additional steps.

The invention claimed is:

1. A process for making an orthopedic implant from cobalt chromium molybdenum alloy, comprising:
   exposing a surface of the implant to pulse plasma nitriding for 10 to 20 hours at approximately 600 degrees Celsius; and
   subsequently coating the implant with a hard material layer using Arc-PVD to form a coated implant, wherein the coating is applied to a thickness of 4.5 μm plus or minus 1.5 μm, and wherein the coated implant has a surface hardness of between 550 and 1300 HV0.1.

2. The process of claim 1, wherein the coated implant has a surface hardness of 1250 HV0.1.

3. The process of claim 1, wherein the coated implant has a hardness depth of between 15 to 50 micrometers.

4. The process of claim 3, wherein the coated implant has a hardness depth of approximately 35 μm.

5. The process of claim 1, wherein the surface of the implant is exposed to pulse plasma nitriding for 16 hours at approximately 600 degrees Celsius.

6. The process of claim 1, wherein the coating is titanium niobium nitride.

7. The process of claim 1, wherein the coating is zirconium nitride.

8. The process of claim 1, wherein the coated implant has a hardness depth of between 15 to 50 micrometers.

9. A process for making an orthopedic implant from alpha-beta titanium alloy, comprising:
   exposing a surface of the implant to pulse plasma nitriding for 10 to 48 hours at approximately 730 to 750 degrees Celsius; and
   subsequently coating the implant with a hard material layer using Arc-PVD to form a coated implant, wherein the coating is applied to a thickness of 4.5 μm plus or minus 1.5 μm, and wherein the coated implant has a surface hardness of between 200 HV0.1 and 1000 HV0.05.

10. The process of claim 9, wherein the coated implant has a surface hardness of approximately 950 HV0.05.

11. The process of claim 9, wherein the coated implant has a hardness depth of between 20 and 70 micrometers.

12. The process of claim 11, wherein the coated implant has a hardness depth of approximately 40 μm.

13. The process of claim 9, wherein the surface of the implant is exposed to pulse plasma nitriding for 16 hours at approximately 730 to 750 degrees celsius.

14. The process of claim 9, wherein the coating is titanium niobium nitride.

15. The process of claim 9, wherein the coating is zirconium nitride.

16. The process of claim 9, wherein the coated implant has a hardness depth of between 20 and 70 micrometers.

* * * * *